United States Patent [19]

Armstrong

[11] Patent Number: 4,468,218
[45] Date of Patent: Aug. 28, 1984

[54] VENTILATION TUBE FOR THE MIDDLE EAR AND METHOD OF IMPLANTING SAME

[76] Inventor: Beverly W. Armstrong, 3034 Hampton Ave., Charlotte, N.C. 28207

[21] Appl. No.: 422,866
[22] Filed: Sep. 24, 1982
[51] Int. Cl.³ .................... A61F 11/00; A61M 27/00
[52] U.S. Cl. .................................. 604/49; 604/165; 604/170; 604/264
[58] Field of Search ............... 128/305, 305.1, 305.3, 128/310; 604/22, 165, 170, 174, 264, 49, 50, 51

[56] References Cited

U.S. PATENT DOCUMENTS

| | | |
|---|---|---|
| D. 224,672 | 8/1972 | Geraci . |
| D. 239,330 | 3/1976 | Shea, Jr. . |
| 3,530,860 | 9/1970 | Majoros . |
| 3,645,268 | 2/1972 | Capote . |
| 3,807,409 | 4/1974 | Paparella et al. . |
| 3,871,380 | 3/1975 | Heros . |
| 3,888,258 | 6/1975 | Akiyama . |
| 3,913,584 | 10/1975 | Walchle et al. . |
| 3,916,873 | 11/1975 | Wasserman . |
| 3,976,081 | 8/1976 | Lapidot . |
| 3,982,545 | 9/1976 | Silverstein . |
| 4,015,607 | 4/1977 | Wright . |
| 4,094,303 | 6/1978 | Johnston . |
| 4,168,697 | 9/1979 | Cantekin . |
| 4,174,716 | 11/1979 | Treace . |
| 4,326,512 | 4/1982 | Peerless . |
| 4,368,738 | 1/1983 | Tersteegen et al. ................ 604/264 |
| 4,405,307 | 9/1983 | Taylor .................................. 604/165 |

OTHER PUBLICATIONS

Richards Microsurgery Catalog Price List No. 1584, Oct. 1, 1982, pp. 3-16.1.
American V. Mueller, Catalog No. 80, p. 680.
Xomed Inc. Catalog, pp. 4-10, 1979.

Primary Examiner—C. Fred Rosenbaum
Assistant Examiner—Michelle N. Lester
Attorney, Agent, or Firm—Bell, Seltzer, Park & Gibson

[57] ABSTRACT

A ventilation tube is disclosed which is adapted to be implanted in the tympanic membrane to ventilate and drain the middle ear. The tube comprises an elongate tubular body, a flange mounted at one end of the body, and the flange includes an incision entry guide portion extending forwardly in a generally axial direction from the remaining portion of the flange, with the guide portion being adapted to initially guide the flange through an incision in the membrane with a minimum of trauma. Also, the ventilation tube includes a notch in the end of the tubular body opposite the flange and which is adapted for cooperation with a mating key on the insertion tool, to facilitate alignment of the guide portion of the flange with the incision during the insertion procedure by precluding relative rotation and tilting between the ventilation tube and insertion tool.

20 Claims, 13 Drawing Figures

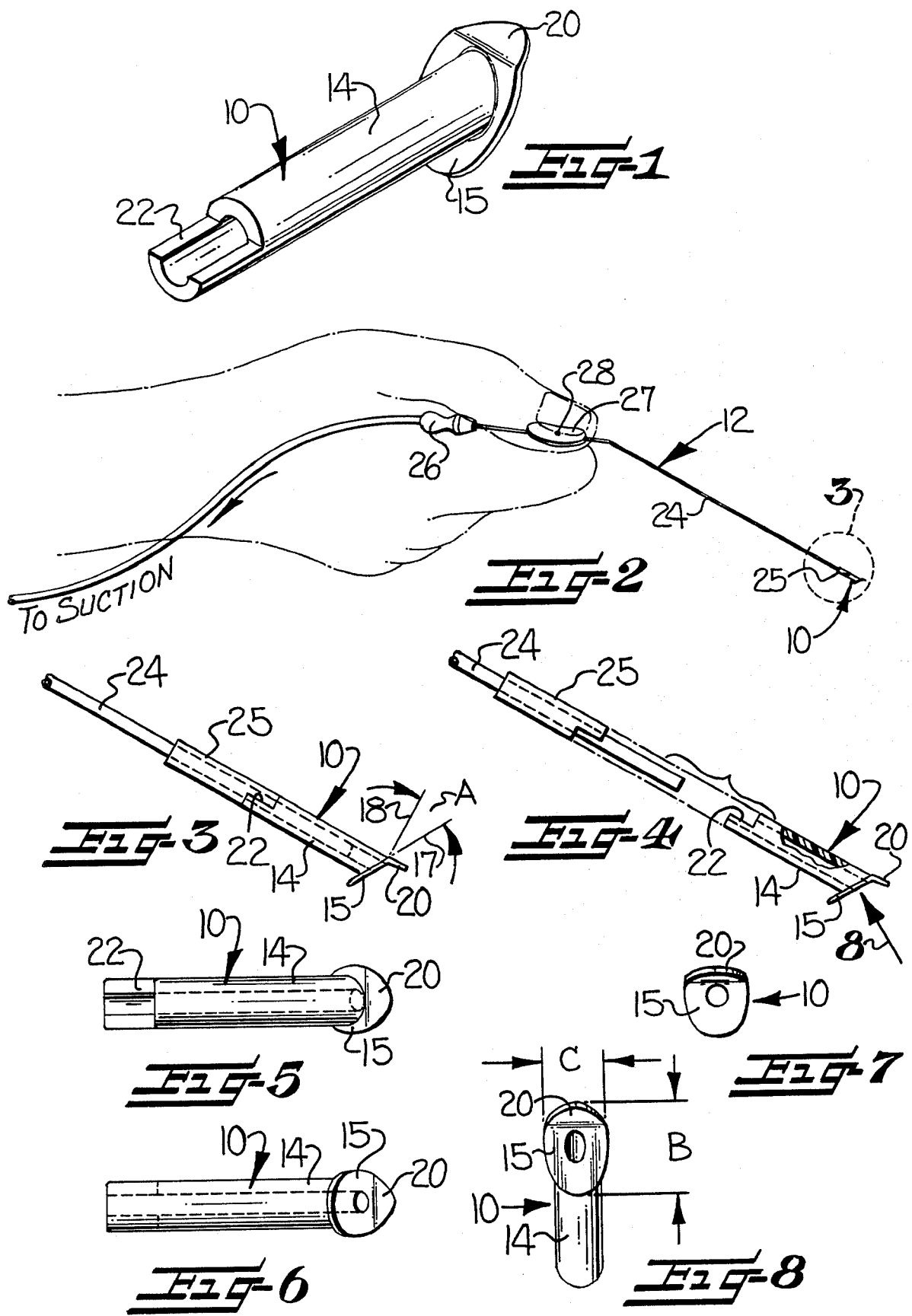

VENTILATION TUBE FOR THE MIDDLE EAR AND METHOD OF IMPLANTING SAME

The present invention relates to a novel ventilation tube adapted to be inserted through and implanted in the tympanic membrane to ventilate and drain the middle ear, and to a method of implanting the tube in the membrane. The invention also relates to a novel insertion tool for supporting the tube during the insertion procedure.

In 1954, the present applicant proposed that a ventilation tube be implanted in the tympanic membrane for the treatment of middle ear disorders, particularly in children; Armstrong, B. W. "A New Treatment for Chronic Secretory Otitis Media", Archives of Otolaryngology 59; 653–654, 1954. Since that time, literally millions of such tubes have been implanted, with excellent results.

Ventilation tubes of the described type have been designed in a variety of configurations. Most typically however, the tube comprises an elongate tubular body, with a flange disposed at one end thereof. To implant the tube, an incision is made in the tympanic membrane, and the end of the tube opposite the flange is gripped by forceps. The thus supported tube is then moved along the auditory canal, with the flanged end disposed forwardly toward the membrane. Upon the flanged end reaching the membrane, the tube is tilted so that the flanged end may enter through the incision. Once inserted, the flange is disposed medial to the membrane, to thereby resist premature withdrawal or extrusion.

In one known tube design, the flange is inclined with respect to the axis of the tubular body to facilitate its insertion. Also, the inclination of the flange results in the opposite end of the tubular body being disposed centrally in the auditory canal, by reason of the anatomy of the tympanic membrane, and the fact that the flange tends to align itself so as to be parallel to the medial side of the membrane. Such central positioning of the opposite end of the tube is desirable in that the opportunity for closure of the tube by the ear fluids and wax, which are often disposed along the walls of the canal, is minimized.

A problem associated with tubes of the above described known designs resides in the fact that it is difficult to align the flanged end of the tube with the incision during the insertion procedure. This difficulty results in part from the very small size of the tube and the attendant difficulty in stabilizing the tube while it is held by forceps. Also, the anatomy of the auditory canal renders it difficult to tilt the tube to align the periphery of the flange with the incision. As a result, tearing and enlargement of the incision during the insertion procedure is common, which not only causes undue trauma, but also renders it more likely for the tube to prematurely withdraw from the membrane.

It is accordingly an object of the present invention to provide a ventilation tube of the described type, and a method of implanting the same, which effectively minimizes trauma during the insertion procedure, and which minimizes the opportunity for the premature extrusion of the tube.

It is a more particular object of the present invention to provide a ventilation tube and method of implanting the same wherein the tube may be accurately guided and stabilized during the insertion procedure, to facilitate its alignment with the incision, and which also includes provision for effectively guiding the flange through the incision.

It is also an object of the present invention to provide a ventilation tube of the described type, and a cooperating insertion tool, wherein the tube is effectively stabilized during the insertion procedure to prevent its inadvertent rotation or tilting with respect to the tool, and wherein the tool permits relatively unobstructed visibility of the tympanic membrane during the insertion procedure.

These and other objects and advantages of the present invention are achieved in the embodiment illustrated herein, by the provision of a ventilation tube which includes an elongate tubular body, a flange mounted at one end of the body, and with the flange including an incision entry guide portion extending forwardly in an axial direction from the remaining portion of the flange. The tube is implanted in the tympanic membrane by a method which includes initially forming an incision in the tympanic membrane, and then mounting the tube on an insertion tool which includes a support rod having a free end which is adapted to slideably receive the tube thereon. The free end of the tool and the supported tube are then moved through the auditory canal, and the incision entry guide portion of the flange is guided through the incision and so that the remaining portion of the flange may follow therethrough with a minimum of trauma.

In the preferred embodiment, the flange is inclined at an angle of at least about 30 degrees with respect to a plane disposed perpendicular to the axis of the body, and the incision entry guide portion is disposed on the portion of the periphery of the flange which is furthest beyond the end of the body which mounts the flange. Also, it is preferred that the opposite end of the body include notch means for cooperation with a mating key or the like on the insertion tool, to further facilitate alignment of the incision entry guide portion with the incision by precluding rotation or tilting of the tube with respect to the insertion tool. The insertion tool may be hollow so that air may be aspirated therethrough during the insertion procedure, to thereby permit fluids to be removed from the vicinity of the tympanic membrane and permit unobstructed visibility in the area of the incision. Also, it is preferred that the support rod of the tool be angled at a medial location along its length to facilitate visibility of the tympanic membrane during the insertion procedure.

Some of the objects of the present invention having been stated, other objects and advantages will appear as the description proceeds, when taken in connection with the accompanying drawing, in which;

FIG. 1 is an enlarged perspective view of a ventilation tube which embodies the features of the present invention;

FIG. 2 is a perspective view of the ventilation tube mounted on an insertion tool in accordance with the present invention;

FIG. 3 is an enlarged perspective view of the tube and the forward or free end of the insertion tool;

FIG. 4 is an exploded perspective view of the tube and the free end of the tool;

FIGS. 5 and 6 are top and bottom plan views of the tube, respectively;

FIG. 7 is a front elevation view of the tube;

FIG. 8 is a perspective view of the tube taken along the direction of the arrow 8 in FIG. 4.

Figure 9:
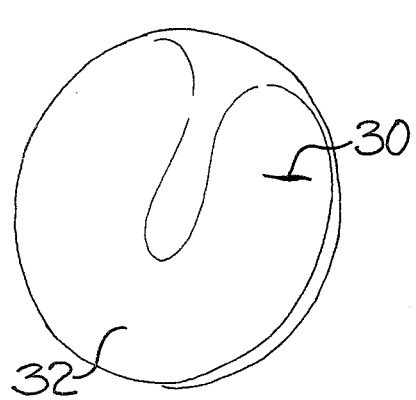
FIGS. 9-13 are somewhat schematic views illustrating the sequence of steps for inserting the tube through the tympanic membrane in accordance with the present invention.

Referring more particularly to the drawings, FIG. 1 illustrates a preferred embodiment of a ventilation tube 10 in accordance with the present invention, and FIG. 2 shows the tube mounted on the forward end of an insertion tool 12. The tube 10 is preferably composed of an integral piece of a suitable plastic material, such as Teflon or silicone, and it includes an elongate tubular body 14, and an outwardly extending flange 15 mounted at one end of the body.

As best seen in FIG. 8, the flange 15 has an oval peripheral outline when viewed frontally, with the body 14 being joined at the center of the flange. In addition, the flange is inclined so as to define a plane 17 which is inclined at an angle A (note FIG. 3) of at least about 30 degrees with respect to a plane 18 disposed perpendicular to the axis of the body. The oval flange defines a major diameter B and a minor diameter C, and the flange is oriented such that its minor axis lies within the plane 18, and the major axis lies along the maximum angle of inclination with respect to the axis of the tubular body and within the plane 17.

The portion of the flange lying on the major axis, and which is furthest beyond the end of the body 14 to which the flange 15 is mounted, is permanently upset or inclined in the forward direction, to define an incision entry guide portion 20. As best seen in FIG. 3, the entry guide portion 20 is substantially flat, and extends forwardly in a direction substantially parallel to the longitudinal axis of the body 14, and forwardly from the most forward portion of the remaining portion of the flange. The incision entry guide portion 20 serves to initially enter the incision in the tympanic membrane as further described below, and to guide the remaining portion of the flange into and through the incision with minimal trauma. The end of the tubular body 14 opposite the flange includes a notch 22 formed in the wall of the body, and for the purposes set forth below.

The tubular body 14 of the tube is cylindrical and has a uniform outer diameter throughout its length, which typically measures about 1.6 mm, and it has an inside diameter of about 1.1 mm. The tube preferably has a length of between about seven to twelve mm, which is sufficient to normally preclude passage of the entire tube inwardly through the tympanic membrane after it has been implanted. The flange 15 typically has a major diameter B of about 3.5 mm, and a minor diameter C of about 2.8 mm, note FIG. 8.

FIGS. 2-4 illustrate a preferred embodiment of an insertion tool 12 for inserting the ventilation tube 10 through an incision in the tympanic membrane. The tool 12 is preferably formed of stainless steel, and it includes an elongate hollow cylindrical support rod 24 which is sized to be closely received in the bore of the tubular body 14 of the ventilation tube. A key 25 is mounted on the support rod at a location spaced a predetermined distance from the forward free end thereof, with such distance generally corresponding to the axial length of the tube 10. The key 25 is designed to be matingly received in the notch 22 at the end of the ventilation tube when the tube is slipped onto the end of the support rod in the illustrated manner. Thus, the interengagement between the key 25 and notch 22 serves to prevent relative rotation between the ventilation tube 10 and support rod 24, and the coaxial placement of the tube on the free end of the support rod prevents tilting of the tube on the rod. It will be noted that the interengagement between the key 25 and the notch 22 automatically orients the tube with respect to the tool 12, as well as the hand and eye of the surgeon, and the incision in the tympanic membrane, as hereinafter further described. The diameter of the support rod 24 is preferably only slightly less than the internal diameter of the bore of the ventilation tube, so that the frictional contact therebetween will tend to retain the ventilation tube on the support rod and prevent its inadvertent removal during normal manipulation of the tool.

The support rod 24 is angled at a medial location along its length, and it is hollow along its full length and communicates with a coupling 26 at the rearward end of the tool 12. The coupling in turn is adapted for operative connection to a vacuum source, whereby air may be aspirated through the rod. Also, there is provided a thumb plate 27 on the tool, which includes an aperture 28 communicating with the central bore of the rod, and such that the aspiration of air through the rod may be controlled by selectively placing the thumb upon the plate to cover and uncover the aperture 28, note FIG. 2.

To now describe the method of implanting the described ventilation tube 10, it will be understood that a relatively short incision 30 is initially formed in the tympanic membrane 32 using a myringotomy knife. As seen in FIG. 9, the incision 30 is preferably formed in the anterior superior quadrant of the membrane, and as close to the anterior margin thereof as possible. Also, the incision should have a length which generally corresponds to the minor diameter C of the flange on the tube to be implanted. The tube 10 is then slipped onto the forward free end of the support rod 24 of the tool in the manner seen in FIGS. 3 and 4, with the key 25 operatively positioned in the notch 22 of the tube.

The forward end of the tool and the retained tube are then moved through the auditory canal, and upon reaching the tympanic membrane, the incision entry guide portion 20 is aligned with the incision 30. If necessary, air may be aspirated through the support rod 24 at this point in time, to remove blood and other debris from the vicinity of the incision 30 and thereby improve visibility. Also, it will be seen that the alignment of the incision entry guide portion 20 with the incision 30 is facilitated by the fact that relative rotation and tilting between the tube and support rod is precluded by the interengagement of the key 25 and slot 22, and the fact that the free end of the rod 24 extends coaxially through a substantial portion of the length of the tube 10. It will also be appreciated that the angled nature of the support rod 24 permits the surgeon to readily sight along the length of the forward portion of the tool 12, to permit a relatively unobstructed view of the tympanic membrane and the tube.

Figure 10:
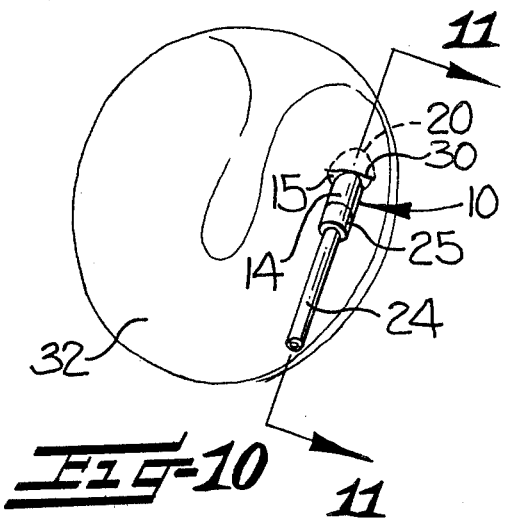
Figure 11:
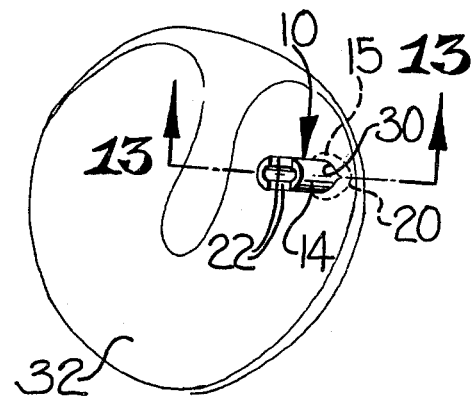
Figure 12:
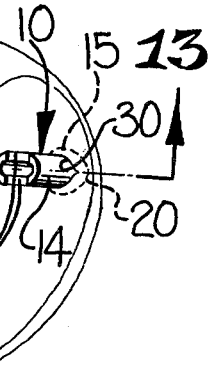
Figure 13:
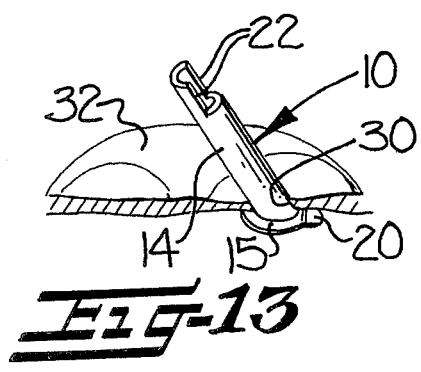

Once the incision entry guide portion 20 is aligned with the incision 30, continued forward movement will cause the guide portion to initially enter through the incision, note FIGS. 10 and 11, followed by the remainder of the flange. Thus, the guide portion 20 serves to guide the entire flange through the incision, with a minimum of trauma. Upon the entire flange being located medially to the membrane, the tool 12 and tube 10 are preferably then rotated 90 degrees so that the major axis of the oval flange is aligned with the incision, note FIG. 12. Since the incision is preferably shorter than the major diameter, the flange cannot readily withdraw back through the incision. Also, in this final position, the flange will tend to align itself adjacent and parallel to the membrane, causing the opposite end of the body to be disposed centrally in the auditory canal. Thus, the opposite end will tend to be spaced from ear fluids and wax which may accumulate along the walls of the canal, and the opportunity for closure of the opposite end by such materials is minimized. As a final step in the insertion procedure, the tool 12 is withdrawn from the auditory canal, causing the tube to slip from its forward end and remain implanted in the membrane 32 in the manner shown in FIGS. 12 and 13.

As a further advantage of the present invention, the notch 22 in the end of the ventilation tube presents a relatively flat projection which may be readily gripped by forceps or the like, when it is later desired to remove the ventilation tube from the membrane, or if forceps are used during the insertion procedure rather than the illustrated tool 12.

In the drawings and specification, there has been set forth a preferred embodiment of the invention, and although specific terms are employed, they are used in a generic and descriptive sense only and not for purposes of limitation.

That which is claimed is:

1. A ventilation tube adapted to be inserted through and implanted in the tympanic membrane to ventilate and drain the middle ear, and characterized by the ability to be readily inserted through the membrane without excessive trauma, and comprising
   an elongate tubular body, and
   a flange mounted at one end of said body, with said flange defining a plane which is inclined at an angle of at least about 30 degrees with respect to a plane disposed perpendicular to the axis of the body, and with said flange including an incision entry guide portion extending forwardly in a direction substantially parallel to the axis of the body and from the most forward portion of the remaining portion of said flange, and whereby during the tube insertion procedure, the incision entry guide portion is adapted to initially enter the incision in the tympanic membrane and guide the remainder of the flange therethrough without significant trauma.

2. The ventilation tube as defined in claim 1 wherein said flange has an oval peripheral outline, with said body being joined substantially at the center of the flange.

3. The ventilation tube as defined in claim 2 wherein the minor axis of said oval flange lies within a plane disposed perpendicular to the axis of the tubular body, and wherein said incision entry guide portion is positioned on the major axis of the flange.

4. The ventilation tube as defined in claim 1 wherein said incision entry guide portion is substantially flat and constitutes an integral portion of said flange which is inclined from the plane defined thereby.

5. The ventilation tube as defined in claim 1 wherein said tube is composed of an integral piece of plastic material.

6. The ventilation tube as defined in claim 1 wherein said tubular body has an axial length at least several times its diameter, and a uniform outer diameter throughout its length.

7. The ventilation tube as defined in claim 6 further comprising notch means formed in the end of said tubular body opposite said flange, and which is adapted for cooperation with a mating key or the like on an insertion tool to facilitate alignment of the incision entry guide portion with the incision during the insertion procedure.

8. A ventilation tube adapted to be inserted through and implanted in the tympanic membrane to ventilate and drain the middle ear, and characterized by the ability to be readily inserted through the membrane without excessive trauma, and comprising
   an elongate tubular body,
   an outwardly extending flange disposed at one end of said body, said flange including an incision entry guide portion extending forwardly in a direction substantially parallel to the axis of the body and from the remaining portion of the flange, and
   notch means at the opposite end of said tubular body for operative engagement with a mating key or the like on an insertion tool,
   whereby during the tube insertion procedure, the incision entry guide portion is adapted to initially enter the incision in the tympanic membrane and guide the remainder of the flange therethrough without significant trauma, and with the notch means being adapted to cooperate with a mating key on the insertion tool to facilitate alignment of the incision entry guide portion with the incision.

9. The ventilation tube as defined in claim 8 wherein said tubular body has an axial length at least several times its diameter and with the length being sufficient to normally preclude passage of the entire tube inwardly through the tympanic membrane.

10. The ventilation tube as defined in claim 8 or 9 wherein said tubular body has a substantially uniform outer diameter throughout its length, and wherein said notch means comprises a notch formed in the wall of said body at said opposite end.

11. A surgical apparatus comprising a ventilation tube adapted to be inserted through and implanted in the tympanic membrane to ventilate and drain the middle ear, and comprising an elongate tubular body, an outwardly extending flange disposed at one end of said body, with said flange including an incision entry guide portion extending forwardly in a direction substantially parallel to the axis of the body and from the remaining portion of the flange, and notch means at the opposite end of said tubular body, and
   an insertion tool comprising an elongate cylindrical support rod, with said rod having a free end which is sized to be closely received in the bore of the tubular body of said ventilation tube, and key means mounted adjacent and spaced from the free end of said rod a distance generally corresponding to the axial length of said ventilation tube for operatively engaging said notch means of the tube,
   whereby said tube is adapted to be coaxially mounted on the free end of said rod with said key means operatively engaging said notch means to prevent relative rotation of the tube on said rod and thereby facilitate alignment of the incision entry guide portion with an incision in the tympanic membrane during the insertion procedure.

12. The surgical apparatus as defined in claim 11 wherein said support rod is tubular, and said tool further comprises coupling means adjacent the end of the rod opposite said free end for connecting the rod to a suction source or the like.

13. The surgical apparatus as defined in claim 12 wherein said support rod includes a thumb plate along its length, and an aperture extending through said thumb plate and communicating with the bore of said tubular rod, whereby a suction drawn through the rod may be selectively controlled by covering and uncovering said aperture.

14. The surgical apparatus as defined in any one of claims 11-13 wherein said support rod of said tool is angled at a medial location along its length to facilitate visibility during the insertion procedure, and the diameter of said free end of said rod is not substantially greater than the bore of said tubular body of said tube and such that the tube will be frictionally retained upon being coaxially mounted on said free end.

15. A method of implanting a ventilation tube in the tympanic membrane to ventilate and drain the middle ear, and comprising the steps of
   providing a ventilation tube comprising an elongate tubular body, a flange mounted at one end of said body, and with said flange including an incision entry guide portion extending forwardly in a direction substantially parallel to the axis of the body and from the remaining portion of the flange,
   forming an incision in the tympanic membrane, and
   inserting the flanged end of the tube through the incision so as to be disposed in the middle ear medially to the membrane, and including initially guiding the incision entry guide portion through the incision so that the flange may be guided therethrough with a minimum of trauma.

16. The method as defined in claim 15 wherein the inserting step includes
   providing an insertion tool having an elongate cylindrical support rod sized to be closely received in the bore of the tubular body of said ventilation tube,
   mounting the ventilation tube coaxially on the support rod of the insertion tool, with the flange adjacent the free end of the support rod, and
   interlocking the tube on said support rod to prevent relative rotation therebetween and thereby facilitate the alignment of said incision entry guide portion with the incision during the inserting step.

17. The method as defined in claim 16 wherein said cylindrical support rod is tubular and the inserting step further includes aspirating air through said support rod so as to remove fluids from the vicinity of the tympanic membrane during the inserting step.

18. The method as defined in any one of claims 15-17 wherein the flange is inclined at an angle of at least about 30 degrees with respect to a plane disposed perpendicularly to the axis of the tubular body, and wherein the incision entry guide portion extends forwardly from the most forward portion of the remaining portion of said flange.

19. The method as defined in claim 18 wherein the flange is of oval peripheral outline, and the incision is formed to have a length generally corresponding to the minor diameter of the oval flange.

20. The method as defined in claim 19 comprising the further step of rotating the tube after the flange has been inserted through the incision so that the major diameter of the flange is aligned with the incision, to thereby resist inadvertent withdrawal of the tube.

* * * * *